US008048975B2

(12) United States Patent
Pacetti

(10) Patent No.: US 8,048,975 B2
(45) Date of Patent: Nov. 1, 2011

(54) AMINO ACID MIMETIC COPOLYMERS AND MEDICAL DEVICES COATED WITH THE COPOLYMERS

(75) Inventor: Stephen Pacetti, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/045,465

(22) Filed: Mar. 10, 2011

(65) Prior Publication Data

US 2011/0160391 A1    Jun. 30, 2011

Related U.S. Application Data

(62) Division of application No. 11/942,705, filed on Nov. 19, 2007, now Pat. No. 7,928,177.

(51) Int. Cl.
*C08F 120/58* (2006.01)
(52) U.S. Cl. ............ 526/304; 526/306; 526/307.7; 526/312; 526/319; 526/328.5
(58) Field of Classification Search .......... 526/304, 526/306, 307.7, 312, 319, 328.5
See application file for complete search history.

(56) References Cited

U.S. PATENT DOCUMENTS

| | | | |
|---|---|---|---|
| 4,141,874 A | | 2/1979 | Oka et al. |
| 4,172,934 A | * | 10/1979 | Heilmann ............ 526/298 |
| 4,668,506 A | | 5/1987 | Bawa |
| 4,931,287 A | | 6/1990 | Bae et al. |
| 5,010,121 A | | 4/1991 | Yeates et al. |
| 5,019,096 A | | 5/1991 | Fox, Jr. et al. |
| 5,155,252 A | | 10/1992 | Yamamoto et al. |
| 5,163,952 A | | 11/1992 | Froix |
| 5,258,020 A | | 11/1993 | Froix |
| 5,607,467 A | | 3/1997 | Froix |
| 5,616,338 A | | 4/1997 | Fox, Jr. et al. |
| 5,674,242 A | | 10/1997 | Phan et al. |
| 5,723,219 A | | 3/1998 | Kolluri et al. |
| 5,780,559 A | * | 7/1998 | Humbert et al. ....... 525/452 |
| 5,824,049 A | | 10/1998 | Ragheb et al. |
| 5,859,174 A | | 1/1999 | Barancyk et al. |
| 5,873,904 A | | 2/1999 | Ragheb et al. |
| 5,879,713 A | | 3/1999 | Roth et al. |
| 5,908,704 A | | 6/1999 | Friedman et al. |
| 5,932,299 A | | 8/1999 | Katoot |
| 5,962,138 A | | 10/1999 | Kolluri et al. |
| 5,997,517 A | | 12/1999 | Whitbourne |
| 6,096,070 A | | 8/2000 | Ragheb et al. |
| 6,110,483 A | | 8/2000 | Whitbourne et al. |
| 6,143,354 A | | 11/2000 | Koulik et al. |
| 6,159,978 A | | 12/2000 | Myers et al. |
| 6,165,338 A | * | 12/2000 | December et al. ........ 204/506 |
| 6,180,632 B1 | | 1/2001 | Myers et al. |
| 6,214,901 B1 | | 4/2001 | Chudzik et al. |
| 6,245,760 B1 | | 6/2001 | He et al. |
| 6,248,129 B1 | | 6/2001 | Froix |
| 6,258,371 B1 | | 7/2001 | Koulik et al. |
| 6,262,034 B1 | | 7/2001 | Mathiowitz et al. |
| 6,270,788 B1 | | 8/2001 | Koulik et al. |
| 6,277,449 B1 | | 8/2001 | Kolluri et al. |
| 6,287,707 B1 | | 9/2001 | Luthra et al. |
| 6,299,604 B1 | | 10/2001 | Ragheb et al. |
| 6,306,176 B1 | | 10/2001 | Whitbourne |
| 6,329,386 B1 | | 12/2001 | Mollison |
| 6,344,035 B1 | | 2/2002 | Chudzik et al. |
| 6,383,196 B1 | | 5/2002 | Bates et al. |
| 6,387,379 B1 | | 5/2002 | Goldberg et al. |
| 6,419,711 B1 | | 7/2002 | Genet et al. |
| 6,475,779 B2 | | 11/2002 | Mathiowitz et al. |
| 6,482,834 B2 | | 11/2002 | Spada et al. |
| 6,524,347 B1 | | 2/2003 | Myers et al. |
| 6,528,526 B1 | | 3/2003 | Myers et al. |
| 6,530,950 B1 | | 3/2003 | Alvarado et al. |
| 6,530,951 B1 | | 3/2003 | Bates et al. |
| 6,613,432 B2 | | 9/2003 | Zamora et al. |
| 6,620,617 B2 | | 9/2003 | Mathiowitz et al. |
| 6,663,662 B2 | | 12/2003 | Pacetti et al. |
| 6,706,819 B1 | | 3/2004 | Araki et al. |
| 6,730,064 B2 | | 5/2004 | Ragheb et al. |
| 6,776,796 B2 | | 8/2004 | Falotico et al. |
| 6,790,228 B2 | | 9/2004 | Hossainy et al. |
| 6,890,583 B2 | | 5/2005 | Chudzik et al. |
| 7,005,137 B1 | | 2/2006 | Hossainy et al. |
| 7,008,667 B2 | | 3/2006 | Chudzik et al. |

(Continued)

FOREIGN PATENT DOCUMENTS

JP          08-059950      *  3/1996

OTHER PUBLICATIONS

U.S. Appl. No. 10/376,348, filed Feb. 26, 2003, Ding et al.
Hunag et al., "Synthesis and Characterization of Self-Assembling Block Copolymers Containing Bioadhesive End Groups", Biomacromolecules 3, pp. 397-406 (2002).
Kocakulak et al., "Investigation of Blood Compatibility of PMEA Coated Extracorporeal Circuits", J. of Bioactive and Compatible Polymers vol. 17, pp. 343-356 (2002).
Lee et al., "Synthesis and Gelation of DOPA-Modified Poly(ethylene glycol) Hydrogels", Biomacromolecules 3, pp. 1038-1047 (2002).
Tanaka et al., "Blood compatible aspects of poly(2-methoxyethylacrylate) (PMEA)-relationship between protein adsorption and platelet adhesion on PMEA surface", Biomaterials 21, pp. 1471-1481 (2000).

(Continued)

*Primary Examiner* — Bernard Lipman
(74) *Attorney, Agent, or Firm* — Squire Sanders & Dempsey, (US) LLP

(57) ABSTRACT

Biocompatible polymers are manufactured to include an amino acid mimetic monomer and one or more hydrophobic acrylate monomers. The amino acid mimetic monomers are selected to mimic the side chain of the amino acids asparagine or glutamine. The amino acid mimetic monomer can be a methacryloyl or acryloyl derivative of 2-hydroxyacetamide, 3-hydroxypropionamide, alaninamide, lactamide, or glycinamide. These amide functional groups offer the advantage of moderate hydrophilicity with little chemical reactivity. The amino acid mimetic monomer can be copolymerized with one or more hydrophobic acrylate monomers to obtain desired coating properties.

15 Claims, 1 Drawing Sheet

U.S. PATENT DOCUMENTS

| | | |
|---|---|---|
| 7,077,859 B2 | 7/2006 | Sirhan et al. |
| 7,094,256 B1 | 8/2006 | Shah et al. |
| 7,217,426 B1 | 5/2007 | Hossainy |
| 7,247,313 B2 | 7/2007 | Roorda et al. |
| 7,396,539 B1 | 7/2008 | Hossainy et al. |
| 7,485,141 B2 | 2/2009 | Majercak et al. |
| 7,560,492 B1 | 7/2009 | Claude et al. |
| 7,563,454 B1 | 7/2009 | Pacetti |
| 7,618,937 B2 | 11/2009 | Messersmith et al. |
| 7,622,533 B2 | 11/2009 | Lee |
| 7,622,537 B2 | 11/2009 | Pacetti |
| 7,700,659 B2 | 4/2010 | Pacetti |
| 7,713,541 B1 | 5/2010 | Pacetti et al. |
| 7,781,551 B2 | 8/2010 | Pacetti et al. |
| 7,910,678 B2 | 3/2011 | Pacetti |
| 7,928,176 B2 | 4/2011 | Pacetti |
| 7,928,177 B2 | 4/2011 | Pacetti |
| 7,974,307 B2 | 7/2011 | Meric |
| 2001/0007083 A1 | 7/2001 | Roorda |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0133183 A1 | 9/2002 | Lentz et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |
| 2004/0034408 A1 | 2/2004 | Majercak et al. |
| 2005/0080212 A1 | 4/2005 | Jing et al. |
| 2006/0216326 A1 | 9/2006 | Pacetti |
| 2007/0010623 A1 | 1/2007 | Ha |
| 2008/0118541 A1 | 5/2008 | Pacetti |
| 2008/0124450 A1 | 5/2008 | Pacetti |
| 2008/0125514 A1 | 5/2008 | Pacetti |
| 2008/0125560 A1 | 5/2008 | Pacetti |
| 2008/0139746 A1 | 6/2008 | Pacetti |
| 2008/0146696 A1 | 6/2008 | Pacetti |
| 2008/0147178 A1 | 6/2008 | Pacetti et al. |
| 2008/0153923 A1 | 6/2008 | Pacetti |
| 2008/0022046 A1 | 9/2008 | Cheng et al. |
| 2011/0160391 A1 | 6/2011 | Pacetti |

OTHER PUBLICATIONS

Dyneon™ Fluorothermoplastics—Product Information (2000).
Hull et al. THV Fluoroplastic in Modern Fluoropolymers ed. J Scheirs 1997 p. 257.
Maccone et al. Macromoelcules 33: pp. 1656-1663 (2000).
Sipos et al. Biomacromolecules 6: pp. 2570-2582 (2005).
Tecnoflon®P 757 (2003).
Trollsas et al., "Hyperbranched Poly(∈-caprolactone) Derived from Interinsically Branched AB2 Macromonomers", Macromolecules 31, pp. 4390-4395 (1998).

* cited by examiner

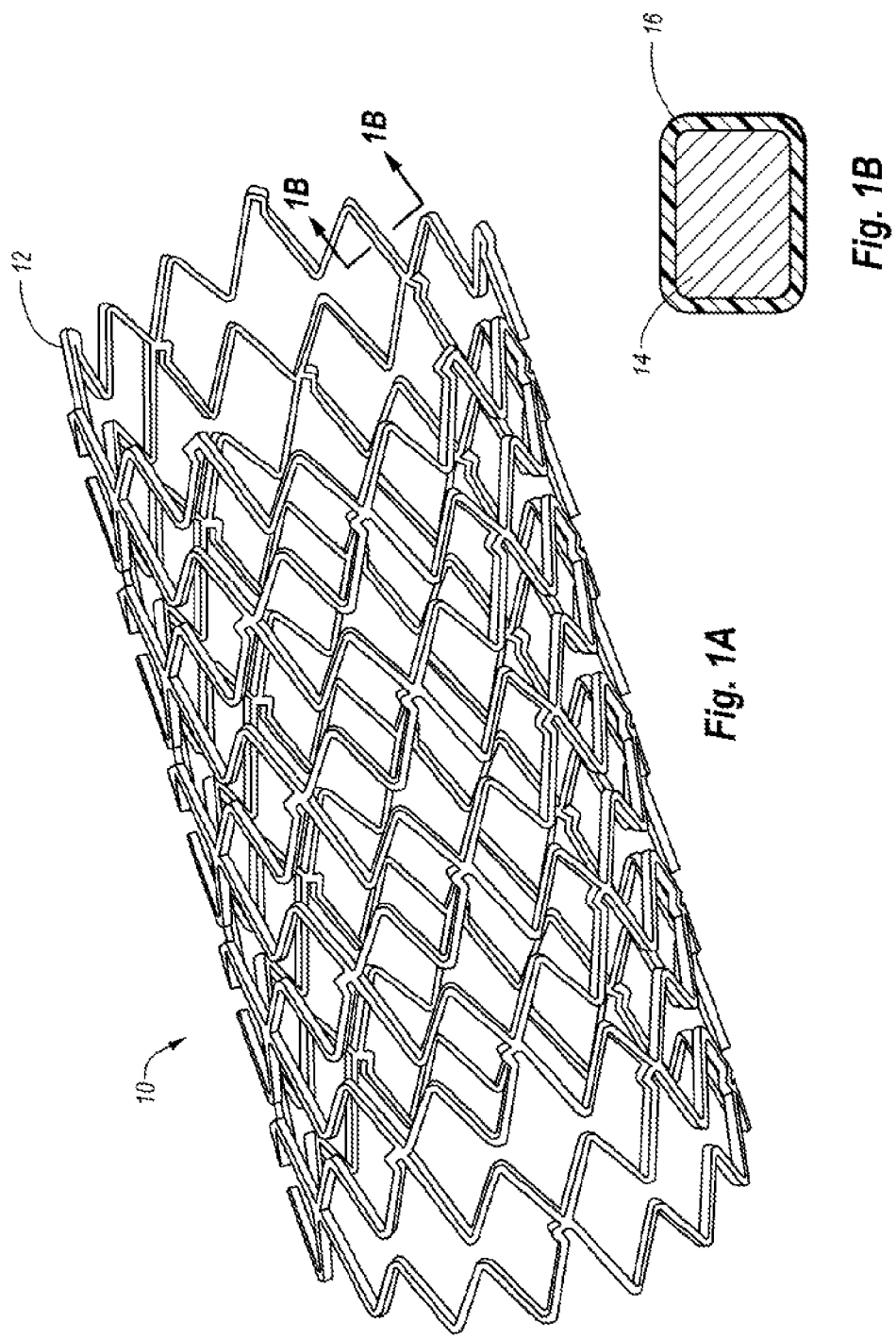

AMINO ACID MIMETIC COPOLYMERS AND MEDICAL DEVICES COATED WITH THE COPOLYMERS

CROSS-REFERENCE TO RELATED APPLICATIONS

This application is a divisional application of U.S. application Ser. No. 11/942,705 filed on Nov. 19, 2007, the teaching of which is incorporated by reference in its entirety. U.S. application Ser. No. 11/942,705 claims the benefit of U.S. Provisional Patent Applications Nos. 60/866,800, 60/866,802, 60/866,804, 60/866,805 60/866,798, 60/866,797, 60/866,796, 60/866,792, all of which were filed on Nov. 21, 2006, and all of which are hereby incorporated by reference in their entirety. This application is related to co-pending U.S. patent application Ser. No. 11,942,695, entitled "Copolymers Having Zwitterionic Moieties and Dihydroxyphenyl Moieties and Medical Devices Coated with the Copolymers", co-pending U.S. patent application Ser. No. 11/942,704, entitled "Methods of Manufacturing Copolymers with Zwitterionic Moieties and Dihydroxyphenyl Moieties and Use of Same", co-pending U.S. patent application Ser. No. 11/942,693, entitled "Zwitterionic Copolymers, Method of Making and Use on Medical Devices", co-pending U.S. patent application Ser. No. 11/942,696, entitled "Methods for Manufacturing Amino Acid Mimetic Copolymers and Use of Same", co-pending U.S. patent application Ser. No. 11/942,700, entitled "Copolymers Having 1-Methyl-2-Methoxyethyl Moieties", and co-pending U.S. patent application Ser. No. 11/942,707, entitled "Methods for Manufacturing Copolymers having 1-Methyl-2-Methoxyethyl Moieties and Use of Same", all of which were filed on Nov. 19, 2007, and all of which are hereby incorporated by reference in their entirety. Co-pending U.S. patent application Ser. No. 11/939,512, filed Nov. 13, 2007, and co-pending application Ser. No. 11/562,338, filed Nov. 21, 2006 are hereby incorporated by reference in their entirety.

BACKGROUND OF THE INVENTION

1. The Field of the Invention

Embodiments of the invention relate to polymeric coatings for coating implantable medical devices. More particularly, embodiments of the invention relate to acrylate copolymers that include monomers that mimic asparagine and glutamine.

2. The Related Technology

Implantable medical devices, including stents, can be coated with polymers to give the implantable device beneficial properties when used in living tissue. Implant coatings, particularly stent coatings, typically need to simultaneously fulfill many criteria. Examples of desirable properties for implant coating properties include: adhesion to the implant (e.g., adhesion to stent struts) to prevent delamination; adequate elongation to accommodate implant deformation without buckling or cracking; sufficient hardness to withstand crimping operations without excessive damage; sterilizability; ability to control the release rate of a drug; biocompatibility including hemocompatibility and chronic vascular tissue compatibility; in the case of durable or permanent coatings, the polymer needs to be sufficiently biostable to avoid biocompatibility concerns; processability (e.g. production of stent coatings that are microns thick); reproducible and feasible polymer synthesis; and an adequately defined regulatory path.

Many methacrylate polymers exhibit several of the forgoing properties. However, some desired properties or combinations of desired properties have been difficult to achieve in methacrylate polymers. For example, homopolymers of hydrophobic methacrylates, including poly(n-butyl methacrylate) (PMBA), can have a low permeability for drugs of interest, leading to a slower drug release rate than desired.

Recently, efforts have been made to copolymerize traditional methacrylate monomers with other monomers to achieve a copolymer that has the benefits of known methacrylate homopolymers and overcomes their deficiencies. One challenge to developing novel methacrylate copolymers has been achieving the desired mechanical properties, and controlling the drug release, while maintaining biocompatibility. Good biocompatibility is essential for patient safety, necessary for device efficacy, and important for receiving regulatory approval to use the polymer on an implantable medical device.

SUMMARY OF THE INVENTION

Embodiments of the invention relate to biocompatible polymers that include an amino acid mimetic monomer and one or more hydrophobic acrylate monomers. The amino acid mimetic monomers are selected to mimic the side chain of the amino acids asparagine or glutamine. Creating synthetic polymers that imitate nature is a form of biomimicry. Mimicking naturally occurring biomolecules is advantageous because it increases the likelihood that the synthetic molecule will be biocompatible. In one embodiment, the amino acid mimetic monomer is a methacryloyl or acryloyl derivative of 2-hydroxyacetamide, 3-hydroxypropionamide, alaninamide, lactamide, or glycinamide. These amide functional groups offer the advantage of moderate hydrophilicity with little chemical reactivity.

The amino acid mimetic monomer is copolymerized with one or more hydrophobic acrylate monomers to obtain the desired coating properties. The hydrophobic monomer provides mechanical strength and moderates water swelling. The amino acid mimetic monomer provides a desired level of hydrophilicity without compromising biocompatibility. The copolymers of the invention can be thermoplastic and mechanically robust, without cross-linking.

These and other advantages and features of the invention will become more fully apparent from the following description and appended claims, or may be learned by the practice of the invention as set forth hereinafter.

BRIEF DESCRIPTION OF THE DRAWINGS

To further clarify the above and other advantages and features of the invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 1A illustrates an example of a stent coated with a copolymer according to one embodiment of the invention; and FIG. 1B is a cross-section of a strut of the stent of FIG. 1A.

DETAILED DESCRIPTION OF EMBODIMENTS OF THE INVENTION

I. Copolymers

The copolymers of the invention include a hydrophobic monomer and a polar monomer that mimics an amino acid.

The combination of the hydrophobic monomer and the amino acid mimetic monomer advantageously provides desired mechanical strength, biocompatibility, and drug permeability in the copolymers of the invention.

For purposes of this invention, the term "acrylate monomer" includes, but is not limited to, methacrylates and acrylates.

The hydrophobic monomer can be a methacrylate or other acrylate monomer that includes hydrophobic groups attached through an ester linkage. The hydrophobic monomer is typically selected to give the copolymer suitable mechanical strength without crosslinking.

Useful hydrophobic monomers are well known. Examples of suitable hydrophobic monomers include, but are not limited to, methyl methacrylate, ethyl methacrylate, n-propyl methacrylate, isopropyl methacrylate, isobutyl methacrylate, sec-butyl methacrylate, 2-ethyl-hexyl methacrylate, n-hexyl methacrylate, cyclohexyl methacrylate, n-hexyl methacrylate, isobornyl methacrylate, trimethylcyclohexyl methacrylate, methyl acrylate, ethyl arylate, n-propyl acrylate, isopropyl acrylate, n-butyl acrylate, isobutyl acrylate, sec-butyl acrylate, pentyl acrylate, n-hexyl acrylate, cyclohexyl acrylate combinations of these, and the like.

The amino acid mimetic monomer is selected so that the resulting polymer possesses protein-like (i.e., polypeptide) properties. Proteins are biological polymers composed of amino acid monomers. The protein molecule derives many of its properties from the side chain or "R group" of the amino acid monomer. The amino acids asparagine and glutamine have polar R groups that are biocompatible, moderately polar, chemically stable, and do not interfere with methacrylate polymer synthesis. The chemical structure of the amino acids asparagine and glutamine are shown below.

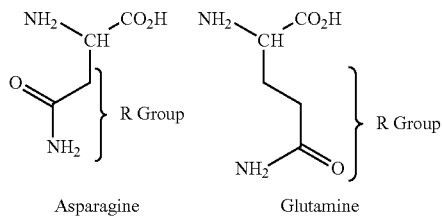

Asparagine    Glutamine

The R group of asparagine is an acetamide group and the R group of glutamine is propionamide. In one embodiment, the amino acid mimetic monomer is an acryloyl or methacryloyl derivative of 2-hydroxyacetamide, 3-hydroxypropionamide. The chemical structures of methacrylate monomers with asparagine and glutamine R groups are shown below.

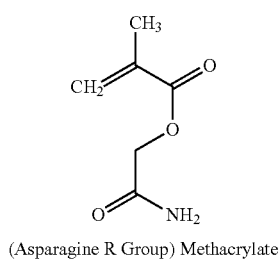

(Asparagine R Group) Methacrylate

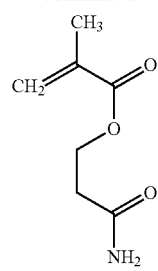

(Glutamine R Group) Methacrylate

The invention can also include acrylate monomers with other acetamide-type R groups that mimic the R group of asparagine or glutamine. Other examples of suitable acetamide-type R groups include alaninamide, lactamide, and glycinamide Examples of monomers with these specific R groups are shown below.

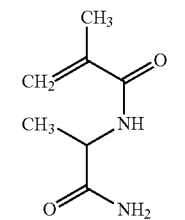

Alaninamide Methacrylate

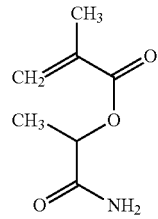

Lactamide Methacrylate

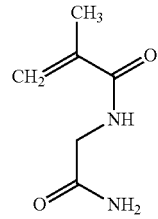

Glycinamide Methacrylate

These methacrylate monomers can be synthesized by conjugating a methacryloyl group with alaninamide, lactamide, and glycinamide, respectively. In an alternative embodiment, the acrylate is synthesized by conjugating an acryloyl group with an alaninamide, lactamide, or glycinamide.

The amino acid mimetic monomers of the invention are polar and biocompatible. Thus, they can advantageously be copolymerized with hydrophobic acrylate monomers. An example of an amino acid mimetic copolymer according to one embodiment of the invention is shown in the following chemical formula.

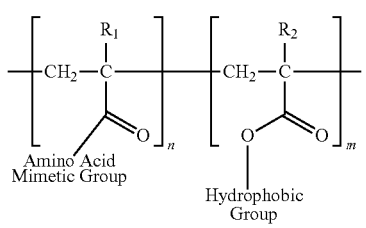

In the forgoing formula, $R_1$ and $R_2$ may be hydrogen or methyl, the amino acid mimetic group can be the conjugation product of 2-hydroxyacetamide, 3-hydroxypropionamide, alaninamide, lactamide, or glycinamide; the hydrophobic group is a straight chain, branched, unsaturated, or cyclic hydrocarbon of one to sixteen carbon atoms; m is in a range from 0.1 to 0.99; and n is in a range from 0.01 to 0.9. Unless otherwise stated, the monomers shown in the chemical formula above and other chemical formulas herein can be in any order within the copolymer molecule and the monomer linkages shown in the chemical formulas only represent that the monomers are part of the same copolymer molecule. Furthermore, unless otherwise stated, the polymeric molecules can include monomers other than those shown in the chemical formulas.

The ratio of amino acid mimetic monomer to hydrophobic monomer is selected to yield a copolymer with sufficient mechanical strength for use as a coating on a medical device. In one embodiment, the concentration of amino acid mimetic monomer is in a range from about 0.5% to about 90% and the concentration of hydrophobic monomer is in a range from about 10% to about 99.5%. The copolymer can be tuned by adjusting the specific monomer ratio to achieve a desired mechanical strength, elongation, and drug permeability.

In one embodiment, the concentration of hydrophobic monomer is selected to yield a thermoplastic copolymer that is substantially free of cross-linking. While cross-linking can prevent excessive water swelling, cross-linking can be disadvantageous because it limits elongation, which leads to cracking of the polymer coating. Another benefit of a thermoplastic system is that it is simple to process compared to thermoset polymers, which reduces manufacturing costs and can improve product quality.

When incorporated into the copolymers of the invention, the amino acid mimetic monomers, and any hydrolysis products that may form in vivo, will be biocompatible since the monomers mimic compounds already present in humans and other animals Thus, the copolymers of the invention are likely to be extremely benign. In addition, the amino acid mimetic monomers make the copolymers of the invention moderately hydrophilic and allow the $T_g$ of the hydrated copolymer to be tuned to a desired temperature. These features are particularly advantageous for drug elution.

II. Methods of Manufacturing

The method of manufacturing the copolymers of the invention generally includes selecting or forming an amino acid mimetic monomer and reacting the amino acid mimetic monomer with a hydrophobic monomer to form a copolymer that is suitable for coating implantable medical devices. By varying the ratio of the hydrophobic monomer to the polar monomer, the properties of the copolymer may be tuned. In one embodiment, the reaction mixture includes 0.5% to 90% of amino acid mimetic monomer and 10% to 99.5% of a hydrophobic monomer, based on the total moles of monomer in the reaction mixture. The type and ratio of monomers is selected to yield a copolymer that is biocompatible and mechanically robust.

The copolymers can be synthesized using free radical polymerization, atom transfer radical polymerization, cationic polymerization, anionic polymerization, iniferter polymerization, or other suitable reactions techniques. Free radical polymerization can be carried out in a solvent using an initiator. Examples of solvents suitable for carrying out the polymerization reaction include alcoholic solvents such as, but not limited to, methanol, ethanol, and isopropyl alcohol. Examples of suitable initiators for carrying out the polymerization reaction include peroxides such as, but not limited to, benzoyl peroxide, and azo compounds. A specific example of a suitable initiator is 2,2'-azo-bis(2-methylproprionitrile). Those skilled in the art are familiar with the conditions for carrying out the foregoing polymerization reactions and other similar polymerization reactions suitable for yielding the copolymers of the invention.

An alternate path to synthesizing the polymer includes copolymerizing methacrylic acid, or acrylic acid, and the hydrophobic monomer to yield a copolymer with the following structure.

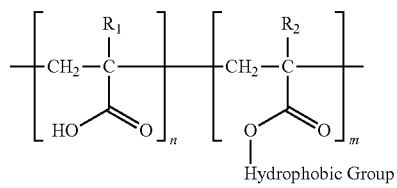

The polymerization reaction to produce this molecule can be carried out using the same polymerization techniques described previously. Next, 2-hydroxyacetamide, 3-hydroxypropionamide, alaninamide, lactamide, or glycinamide, or other suitable acetamide group is coupled to the carboxy groups of the methacrylic or acrylic acid. Several coupling chemistries can be used to perform the coupling reaction, including, but not limited to, conversion to an acid chloride or use of carbodiimides. For the coupling of amino acid mimetic groups with amine functional groups, an example method is to form the n-hydroxysuccinimidyl ester of the polymer by coupling N-hydroxysuccinamide with dicyclohexyl carbodiimide (DCC). The amino-functional amino acid mimetic group such as, but not limited to glycinamide, can then be coupled to the activated carboxyl group. An example of a technique that can be used to couple the hydroxyl functional moieties is DCC and 4-(dimethylamino)pyridinium (DPTS) as described in M. Trollsas, J. Hedrick, Macromolecules 1998, 31, 4390-4395.

In yet another alternative embodiment, the amino acid mimetic monomer can be synthesized by first forming a homopolymer of a hydrophobic monomer. The homopolymer can then be subjected to acid catalysis with an acetamide acid such as, but not limited to 2-hydroxyacetamide. This reaction exchanges some of the hydrophobic groups as ethanol and replaces them with the acetamide group by transesterification. Byproducts, including ethanol, can be removed by distillation, for example.

In one embodiment, the copolymer compositions are manufactured to have a desired $T_g$ when hydrated. The $T_g$ of the copolymer can be calculated by knowing the amount of water absorbed and the $T_g$ derived from measurements of the homopolymer of the respective monomers. In an embodiment, the $T_g$ is calculated using the Fox equation, which is shown below.

$$\frac{1}{T_g^{Polymer}} = \frac{W^{PC}}{T_g^{PC}} + \frac{W^{Water}}{T_g^{Water}} + \frac{W^{Methacrylate}}{T_g^{Methacrylate}}$$

$T_g$=Glass transition temperature of the homopolymer or pure material.
$T_g^{water}$=-40° C.
W=Weight fraction of the components.

Once the water absorption of the polymer is known, which is usually measured experimentally, the copolymer $T_g$ can be estimated with the desired target. In one embodiment the desired target $T_g$ is in a range from about −30° C. to about 37° C. when in the fully hydrated state. In another range, the $T_g$ is between about 0° C. and about 37° C. when hydrated. With a $T_g$ of less than 37° C., the copolymers of the invention will have a high degree of polymer mobility when placed in vivo. This feature allows the surface of the polymer to enrich in hydrophilic monomer content, which is advantageous for biocompatibility.

In an alternative embodiment, the co-polymer is designed to have a desired $T_g$ for the polymer in the dry state. In an embodiment, the $T_g$ of the polymer when dry is in a range from about −30° C. to about 100° C. or alternatively in a range from 0° C. to about 70° C.

The polymerization reaction can be controlled to produce the copolymers with a desired molecular weight. In one embodiment, the number average molecular weight of the copolymer is in the range from about 20K to about 800K, and in another range from about 100K to about 600K.

In an alternative embodiment, the molecular weight of the polymer is selected to provide adhesion. In this embodiment, the number average molecular weight can be in a range from about 2K to about 200K. The adhesive polymer can be used on medical devices that benefit from an adhesive polymer coating.

In an embodiment, the copolymers are manufactured substantially free of cross-linking. Copolymers manufactured according to the invention can have sufficient mechanical strength when hydrated that cross-linking is not necessary for making a polymer coating suitable for coating an implantable device. The absence of cross-linking in the copolymers of the invention gives the copolymers improved elasticity, particularly when dry, which reduces the likelihood of cracking during assembly and use.

III. Use of Coatings on Implantable Devices

The foregoing copolymers are suitable for use on any medical device that is compatible with polymer coatings. The copolymers can be used alone as a coating or can be combined with other polymers or agents to form a polymer coating. For example, the polymers may be blended with poly(vinyl pyrrolidinone), poly(n-butyl methacrylate), poly(n-butyl methacrylate) copolymers, methacrylate polymers, acrylate polymers, and/or a terpolymers of hexyl methacrylate, vinyl acetate, and vinyl pyrrolidinone.

The polymer coatings can be applied to a medical device using any techniques known to those skilled in the art or those that may be developed for applying a coating to a medical device. Examples of suitable techniques for applying the coating to the medical device include spraying, dip coating, roll coating, spin coating, powder coating, inkjet printing, and direct application by brush or needle. One skilled in the art will appreciate the many different techniques in powder coating. The copolymers can be applied directly to the surface of the implant device, or they can be applied over a primer or other coating material.

In one embodiment, the polymer coating is applied to a medical device using a solvent-based technique. The polymer can be dissolved in the solvent to form a solution, which can be more easily applied to the medical device using one or more of the above mentioned techniques or another technique. Thereafter substantially all or a portion of the solvent can be removed to yield the polymer coating on a surface of the medical device.

Examples of suitable solvents that can be used with the copolymers of the invention include, but are not limited to, dimethylacetamide (DMAC), dimethylformamide (DMF), tetrahydrofuran (THF), dimethylsulfoxide (DMSO), cyclohexanone, xylene, toluene, acetone, n-butanol, i-propanol, methyl ethyl ketone, propylene glycol monomethyl ether, methyl t-butyl ketone, methyl isobutyl ketone, ethyl acetate, n-butyl acetate, ethanol, methanol, chloroform, trichloroethylene, 1,1,1-trichloroethane, methylene chloride, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); and 1,1,2-trichloroethane and chloroform (80:20 w/w).

Examples of suitable implantable devices that can be coated with the copolymers of the invention include coronary stents, peripheral stents, catheters, arterio-venous grafts, by-pass grafts, pacemaker and defibrillator leads, anastomotic clips, arterial closure devices, patent foramen ovale closure devices, and drug delivery balloons The copolymers are particularly suitable for permanently implanted medical devices.

The implantable device can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-chromium-nickel and cobalt-chromium-tungsten alloys). Suitable nonmetallic biocompatible materials include, but are not limited to, polyamides, fluoropolymers, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, c-caprolactone, and the like, and combinations of these).

The copolymers are particularly advantageous as a coating for stents due to their elongation properties, which allow the coated stent to be crimped and expanded without cracking the coating. The stents can be composed of wire structures, flat perforated structures that are subsequently rolled to form tubular structures, or cylindrical structures that are woven, wrapped, drilled, etched or cut.

FIG. 1A shows an example stent 10 coated with a copolymer including amino acid mimetic monomers. Stent 10 includes a generally tubular body 12 with a lumen. The struts of body 12 (e.g. strut 14) provide a supporting structure for coating the polymers of the invention.

FIG. 1B illustrates a cross-section of the stent of FIG. 1A coated with a polymer coating 16 according to an embodiment of the invention. The polymer coating 16 can be conformal as in FIG. 1B. Alternatively, the coating can be ablumenal, luminal, or any combination thereof. In one embodiment, the copolymers of the invention can be elastic at body temperatures and can therefore expand without cracking as the stent expands during use.

The polymer coated stents of the invention can be self-expanding or balloon expandable. The copolymer coatings of the invention can be particularly advantageous for self-expanding stents. Self-expanding stents are typically restrained by a sheath that is removed during deployment of the stent. The copolymers of the invention have improved mechanical strength to better withstand the friction exerted on the polymer as the sheath is removed.

In one embodiment, a bioactive agent is associated with the coated medical devices. The bioactive agent can be associated with a base coat, top coat, mixed with the novel copolymers of the invention, and/or incorporated or otherwise applied to a supporting structure of the medical device.

The bioactive agent can have any therapeutic effect. Examples of suitable therapeutic properties include anti-proliferative, anti-inflammatory, antineoplastic, antiplatelet, anti-coagulant, anti-fibrin, antithrombonic, antimitotic, antibiotic, antiallergic and antioxidant properties.

Examples of suitable bioactive agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents, including streptokinase and tissue plasminogen activator, antigens, hormones, growth factors, ribozymes, retroviral vectors, anti-proliferative agents including rapamycin (sirolimus), 40-O-(2-hydroxyethyl)rapamycin (everolimus), 40-O-(3-hydroxypropyl)rapamycin, 40-O-(2-hydroxyethoxy)ethylrapamycin, 40-O-tetrazolylrapamycin (zotarolimus, ABT-578), 40-epi-(N1-tetrazolyl)-rapamycin, 40-O-[2-(2-hydroxy)ethoxy]ethyl-rapamycin, Biolimus A9 (biosensors International, Singapore), deforolimus, AP23572 (Ariad Pharmaceuticals), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax ä, calcium channel blockers including nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements including vitamins, anti-inflammatory agents including aspirin, tacrolimus, dexamethasone, dexamethasone acetate, dexmethasone phosphate, momentasone, cortisone, cortisone acetate, hydrocortisone. prednisone, prednisone acetate, betamethasone, betamethasone acetate, clobetasol, cytostatic substances including angiopeptin, angiotensin converting enzyme inhibitors including captopril, cilazapril or lisinopril, antiallergic agents is permirolast potassium, alpha-interferon, bioactive RGD, and genetically engineered epithelial cells. Other bioactive agents which are currently available or that may be developed in the future for use with drug eluting stents may likewise be used and all are within the scope of this invention.

The medical devices of the invention can be used in any vascular, tubular, or non-vascular structure in the body. In an embodiment, a coated stent can be used in, but is not limited to use in, neurological, carotid, coronary, aorta, renal, biliary, ureter, iliac, femoral, and popliteal vessels.

IV. EXAMPLES

The following are specific examples of copolymers of amino acid mimetic monomers and hydrophobic monomers. The following copolymers are useful for coating implantable medical devices.

Example 1

Example 1 describes a copolymer of poly(acetamide methacrylate-co-n-butyl methacrylate). The polymer has the following formula.

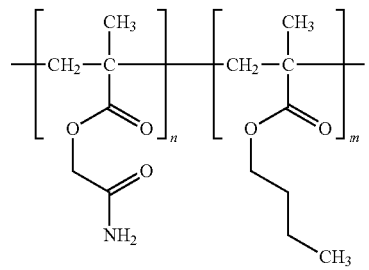

In the foregoing formula, m is in a range from 0.1 to 0.99 and n is in a range from 0.01 to 0.9. The use of poly(n-butyl methacrylate) monomer is particularly advantageous since the homopolymer of PBMA is currently being used in implantable medical devices and is thus known to be biocompatible.

Example 2

Example 2 describes a copolymer of poly(3-methacryloyl propionamide-co-ethyl methacrylate). The chemical formula of poly(3-methacryloyl propionamide-co-ethyl methacrylate) is shown below.

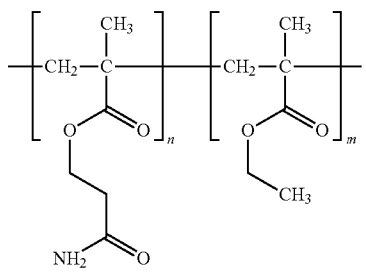

In the foregoing formula, m is in a range from about 0.1 to about 0.98 and n is in a range from about 0.02 to about 0.9. The higher $T_g$ of the alkyl methacrylate monomer will enable a harder, stronger coating at the expense of elasticity as compared to Example 1.

Example 3

Example 3 describes a copolymer of poly(alaninamide methacrylate-co-n-propyl methacrylate). The copolymer of Example 3 has the following formula.

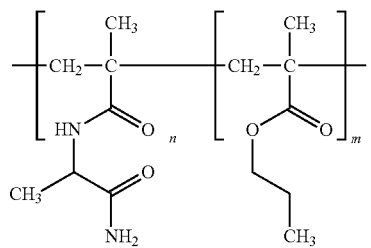

In the foregoing formula, m is in a range from about 0.1 to about 0.995 and n is in a range from about 0.005 to about 0.9.

Example 4

Example 4 describes a copolymer of poly(lactamide methacrylate-co-n-butyl methacrylate). The copolymer of Example 4 has the following formula.

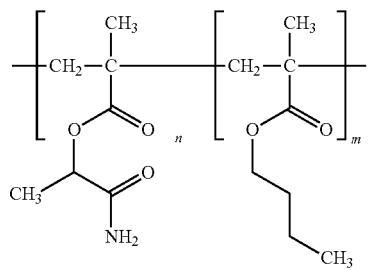

In the foregoing formula, m is in a range from about 0.1 to about 0.995 and n is in a range from about 0.005 to about 0.9. The use of poly(n-butyl methacrylate) monomer is particularly advantageous since the homopolymer of PBMA is currently being used in implantable medical devices and is thus known to be biocompatible.

Example 5

Example 5 describes a copolymer of poly(glycinamide methacrylate-co-n-hexyl methacrylate). The copolymer of Example 5 has the following formula.

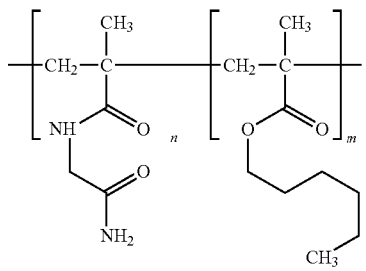

In the foregoing formula, m is in a range from about 0.1 to about 0.995 and n is in a range from about 0.005 to about 0.9.

Example 6

Example 6 describes a method for manufacturing a coated stent using one or more of the polymers of Examples 1-5. In a first step, a primer coating is applied to the stent. A primer solution including between about 0.1 mass % and about 15 mass %, (e.g., about 2.0 mass %) of poly(n-butyl methacrylate) (PBMA) and the balance, a solvent mixture of acetone and cyclohexanone (having about 70 mass % of acetone and about 30 mass % of cyclohexanone) is prepared. The solution is applied onto a stent to form a primer layer.

To apply the primer layer, a spray apparatus, (e.g., Sono-Tek MicroMist spray nozzle, manufactured by Sono-Tek Corporation of Milton, N.Y.) is used. The spray apparatus is an ultrasonic atomizer with a gas entrainment stream. A syringe pump is used to supply the coating solution to the nozzle. The composition is atomized by ultrasonic energy and applied to the stent surfaces. A useful nozzle to stent distance is about 20 mm to about 40 mm at an ultrasonic power of about one watt to about two watts. During the process of applying the composition, the stent is optionally rotated about its longitudinal axis, at a speed of 100 to about 600 rpm, for example, about 400 rpm. The stent is also linearly moved along the same axis during the application.

The primer solution is applied to a 15 mm Triplex, N stent (available from Abbott Vascular Corporation) in a series of 20-second passes, to deposit, for example, 20 ug of coating per spray pass. Between the spray passes, the stent is allowed to dry for about 10 seconds to about 30 seconds at ambient temperature. Four spray passes can be applied, followed by baking the printer layer at about 80° C. for about 1 hour. As a result, a primer layer can be formed having a solids content of about 80 μg. For purposes of this invention, "Solids" means the amount of the dry residue deposited on the stent after all volatile organic compounds (e.g., the solvent) have been removed.

In a separate step, a copolymer solution is prepared. The copolymer solution includes one or more of the copolymer of Examples 1, 2, 3, 4, or 5. The solution is prepared by dissolving between about 0.1 mass % and about 15 mass %, (e.g., about 2.0 mass %) of the copolymer in a solvent. The solvent can be a mixture of about 50 mass % ethanol and about 50 mass % n-butanol.

In a manner similar to the application of the primer layer, the copolymer solution is applied to a stent. Twenty one spray passes are performed with a coating application of 10 μg per pass, with a drying time between passes of 10 seconds, followed by baking the copolymer layer at about 60° C. for about 1 hour, to form a layer having a solids content between about 30 µg and 750 µg, (e.g., about 210 µg).

Example 7

Example 7 describes a method for manufacturing a drug eluting stent according to an embodiment of the invention. The medical device is manufactured using the same method as in Example 6, except that instead of the copolymer solution, a polymer-therapeutic solution is prepared and applied using the following formula.

A drug-including formulation is prepared that includes:
(a) between about 0.1 mass % and about 15 mass %, (e.g., about 2.0 mass %) of the copolymer of one or more of Example 1-5;
(b) between about 0.1 mass % and about 2 mass %, for example, about 1.0 mass % of a therapeutic agent. In one embodiment, the therapeutic agent is ABT-578 (available from Abbott Vascular Corp. of Chicago, Ill.); and
(c) the balance, a solvent mixture including about 50 mass % of ethanol and about 50 mass % of n-butanol.

The drug-including formulation is applied to the stent in a manner similar to the application of the copolymer solution in Example 6. The process results in the formation of a drug-polymer reservoir layer having a solids content between about 30 µg and 750 µg, (e.g., about 210 µg) and a drug content of between about 10 µg and about 250 µg, (e.g., about 70 µg).

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A medical device comprising a supporting structure having a coating associated therewith, the coating comprising a polymer having the formula,

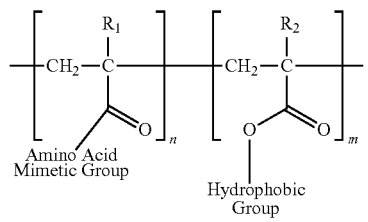

in which,
the hydrophobic group is a straight chain, branched, unsaturated or cyclic hydrocarbon of one to sixteen carbon atoms;
in which the amino acid mimetic group is selected from the group consisting of acetamide, propionamide, alaninamide, lactamide, glycinamide, or a combination thereof
$R_1$ and $R_2$ are independently a hydrogen or a methyl group;
m is in a range from about 0.1 to about 0.995; and
n is in a range from about 0.005 to about 0.9.

2. The implant device coating as in claim 1, in which the amino acid mimetic group is selected from the group consisting of acetamide, propionamide, alaninamide, lactamide, and glycinamide.

3. The medical device as in claim 1, in which the hydrophobic group is selected from the group consisting of a methyl, ethyl, n-propyl, isopropyl, n-butyl, isobutyl, sec-butyl, 2-ethyl-hexyl, n-hexyl, cyclohexyl, n-hexyl, isobornyl, or trimethylcyclohexyl, and combinations thereof.

4. The medical device as in claim 1, in which $R_1$ and $R_2$ are methyl groups.

5. The medical device as in claim 1, in which the glass transition temperature of the polymer when hydrated is in a range from about −30° C. to about 37° C.

6. The medical device as in claim 1, in which the glass transition temperature of the polymer when dry is in a range from about −30° C. to about 100° C.

7. The medical device as in claim 1, in which the polymer having a chemical formula of

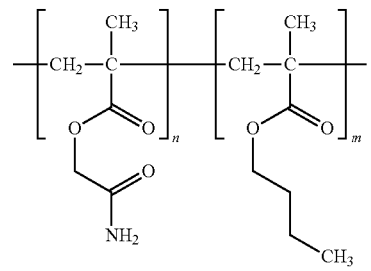

in which,
m is in a range from about 0.1 to about 0.995;
n is in a range from about 0.005 to about 0.9; and
m+n=1.

8. The medical device as in claim 1, in which the polymer having a chemical formula of

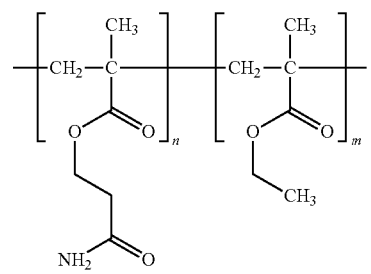

in which,
m is in a range from about 0.1 to about 0.995;
n is in a range from about 0.005 to about 0.9; and
m+n=1.

9. The medical device as in claim 1, wherein the polymer having a chemical formula of

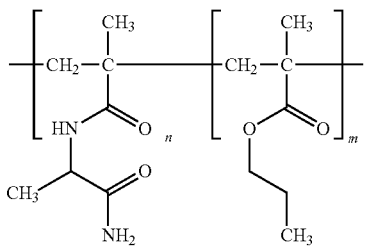

in which,
- m is in a range from about 0.1 to about 0.995;
- n is in a range from about 0.005 to about 0.9; and
- m+n=1.

10. The medical device as in claim 1, in which the polymer having a chemical formula of

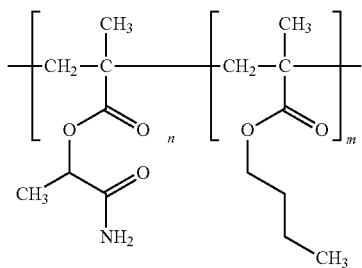

in which,
- m is in a range from about 0.1 to about 0.995;
- n is in a range from about 0.005 to about 0.9; and
- m+n 1.

11. The medical device as in claim 1, in which the polymer having a chemical formula of

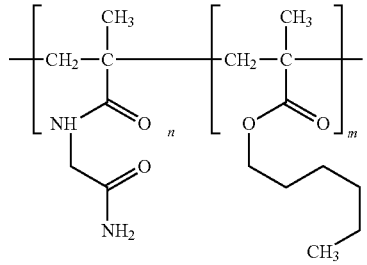

in which,
- m is in a range from about 0.1 to about 0.995; and
- n is in a range from about 0.005 to about 0.9.

12. The medical device as in claim 1, in which the number average molecular weight of the polymer is in a range from about 20K to about 800K.

13. The medical device as in claim 1, in which the number average molecular weight of the polymer is in a range from about 100K to about 600K.

14. The medical device as in claim 1, in which the number average molecular weight of the polymer is in a range from about 2K to about 200K.

15. The medical device as in claim 1, in which the polymer is substantially free of cross-linking.

* * * * *